US009982286B2

(12) United States Patent
Reiter et al.

(10) Patent No.: US 9,982,286 B2
(45) Date of Patent: *May 29, 2018

(54) MEDIUM FOR THE PROTEIN-FREE AND SERUM-FREE CULTIVATION OF CELLS

(71) Applicants: Baxalta Incorporated, Bannockburn, IL (US); Baxalta GmbH, Glattpark (Opfikon) (CH)

(72) Inventors: Manfred Reiter, Vienna (AT); Wolfgang Mundt, Vienna (AT); Friedrich Dorner, Vienna (AT); Leopold Grillberger, Vienna (AT); Artur Mitterer, Orth/Donau (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 4 days.

This patent is subject to a terminal disclaimer.

(21) Appl. No.: 15/235,453

(22) Filed: Aug. 12, 2016

(65) Prior Publication Data

US 2016/0369316 A1  Dec. 22, 2016

Related U.S. Application Data

(63) Continuation of application No. 14/231,221, filed on Mar. 31, 2014, now Pat. No. 9,441,203, which is a continuation of application No. 13/198,476, filed on Aug. 4, 2011, now Pat. No. 8,722,406, which is a continuation of application No. 11/841,915, filed on Aug. 20, 2007, now Pat. No. 8,021,881, which is a continuation of application No. 10/405,794, filed on Apr. 1, 2003, now abandoned, which is a continuation of application No. 09/672,240, filed on Sep. 28, 2000, now abandoned.

(30) Foreign Application Priority Data

Sep. 28, 1999 (AT) ..................................... A1659/99

(51) Int. Cl.
*C12N 5/02* (2006.01)
*C12P 21/00* (2006.01)
*C12N 5/071* (2010.01)
*C12N 5/00* (2006.01)
*C07K 14/755* (2006.01)

(52) U.S. Cl.
CPC ............ *C12P 21/00* (2013.01); *C07K 14/755* (2013.01); *C12N 5/005* (2013.01); *C12N 5/0037* (2013.01); *C12N 5/0043* (2013.01); *C12N 5/0682* (2013.01); *C12N 2500/05* (2013.01); *C12N 2500/32* (2013.01); *C12N 2500/38* (2013.01); *C12N 2500/46* (2013.01); *C12N 2500/60* (2013.01); *C12N 2500/76* (2013.01); *C12N 2500/92* (2013.01)

(58) Field of Classification Search
CPC .................................................. C12N 5/0037
See application file for complete search history.

(56) References Cited

U.S. PATENT DOCUMENTS

| | | |
|---|---|---|
| 4,431,629 A | 2/1984 | Olsen |
| 4,443,540 A | 4/1984 | Chervan et al. |
| 4,767,704 A | 8/1988 | Cleveland et al. |
| 4,978,616 A | 12/1990 | Dean, Jr. et al. |
| 5,024,947 A | 6/1991 | Inlow et al. |
| 5,122,469 A | 6/1992 | Mather et al. |
| 5,316,938 A | 5/1994 | Keen et al. |
| 5,356,798 A | 10/1994 | Kongerslev et al. |
| 5,378,612 A | 1/1995 | Nakashima et al. |
| 5,393,668 A | 2/1995 | Cinati et al. |
| 5,441,868 A | 8/1995 | Lin |
| 5,573,937 A | 11/1996 | Shinmoto et al. |
| 5,633,162 A | 5/1997 | Keen et al. |
| 5,719,050 A | 2/1998 | Hashimoto et al. |
| 5,741,705 A | 4/1998 | Blom et al. |
| 5,789,247 A | 8/1998 | Ballay et al. |
| 5,804,420 A | 9/1998 | Chan et al. |
| 5,811,299 A | 9/1998 | Renner et al. |
| 5,851,800 A | 12/1998 | Adamson et al. |
| 5,885,835 A | 3/1999 | Blom et al. |
| 6,048,728 A | 4/2000 | Inlow et al. |
| 6,100,061 A | 8/2000 | Reiter et al. |
| 6,475,725 B1 | 11/2002 | Reiter et al. |
| 7,094,574 B2 | 8/2006 | Reiter et al. |
| 8,603,777 B1 | 12/2013 | Hagen et al. |
| 2002/0182679 A1 | 12/2002 | Reiter et al. |
| 2003/0203448 A1 | 10/2003 | Reiter et al. |

FOREIGN PATENT DOCUMENTS

| | | |
|---|---|---|
| AT | 1659/99 | 9/1999 |
| AU | 78958/98 | 10/1998 |
| AU | 199953636 | 3/2001 |

(Continued)

OTHER PUBLICATIONS

"Technical Resources: 32500—DMEM/F-12, powder," [Retrieved from the Internet on Aug. 18, 2016], URL<http://www.lifetechnologies.com/us/en/home/technical-resources/media-formulation.218.html>, 3 pages.
AstraZeneca AB Opposition Brief to European Patent No. 1200561, dated Mar. 14, 2007.
Bayer Healthcare AG Opposition Brief to European Patent No. 1200561, dated Mar. 13, 2007.
BD Bionutrients™; Technical Manual Advanced Bioprocessing Third Edition Revised Oct. 2006, pp. 1-67.
Berg, D.T. et al., "High-Level Expression of Secreted Proteins from Cells Adapted to Serum-Free Suspension Culture"; Bio Techniques; 1993; Vo. 14(6); pp. 972-978.
Bielicki, J. et al., "Recombinant Human Sulphamidase: Expression, Amplification, Purification and Characterization"; 1998; Biochem. J.; vol. 329; pp. 145-150.
Bioceuticals Arzneimittel AG Opposition Brief to European Patent No. 1200561, dated Mar. 14, 2007.
Biochrom AG; Dulbecco's MEM (DMEM) Formulation Information, 1 page.
Biochrom AG; Dulbecco's MEM Formulation Information (German Version), 1 page.
Biochrom AG; Dulbecco's MEM/HAM' s F-12 (1:1) Formulation Information (German Version), 1 page.

(Continued)

*Primary Examiner* — Allison M Fox
(74) *Attorney, Agent, or Firm* — Morgan, Lewis & Bockius LLP; Christopher J. Betti

(57) ABSTRACT

A medium is described for the protein-free and serum-free cultivation of cells, especially mammalian cells, whereby the medium contains a proportion of soy hydrolysate.

11 Claims, 4 Drawing Sheets

(56) References Cited

FOREIGN PATENT DOCUMENTS

| | | |
|---|---|---|
| CA | 2161517 | 11/1994 |
| EP | 0160457 | 11/1985 |
| EP | 0241210 | 10/1987 |
| EP | 0481791 | 4/1992 |
| EP | 0485689 | 5/1992 |
| EP | 0631731 | 1/1995 |
| EP | 0666312 | 8/1995 |
| EP | 0711835 | 5/1996 |
| EP | 0872487 | 10/1998 |
| EP | 00120896.6 | 9/2000 |
| EP | 1200561 | 6/2006 |
| FR | 2196386 | 3/1974 |
| JP | 3-244391 | 10/1991 |
| JP | 4-316484 | 11/1992 |
| JP | 5-123178 | 5/1993 |
| JP | 7-039386 | 2/1995 |
| JP | 2057176 | 3/1996 |
| JP | 9107955 | 4/1997 |
| JP | 2-859679 | 2/1999 |
| JP | H01-211488 | 8/1999 |
| RU | 2122583 | 11/1998 |
| WO | 85/02610 | 6/1985 |
| WO | 86/04920 | 8/1986 |
| WO | 88/00967 | 2/1988 |
| WO | 89/00192 | 1/1989 |
| WO | 91/09122 | 6/1991 |
| WO | 91/09935 | 7/1991 |
| WO | 91/10726 | 7/1991 |
| WO | 94/25599 | 11/1994 |
| WO | 96/07730 | 3/1996 |
| WO | 96/15231 | 5/1996 |
| WO | 96/18734 | 6/1996 |
| WO | 96/26266 | 8/1996 |
| WO | 96/40866 | 12/1996 |
| WO | 97/05240 | 2/1997 |
| WO | 97/37547 | 10/1997 |
| WO | 98/08934 | 3/1998 |
| WO | 98/15614 | 4/1998 |
| WO | 98/36051 | 8/1998 |
| WO | 98/54296 | 12/1998 |
| WO | 99/05268 | 2/1999 |
| WO | 99/47648 | 9/1999 |
| WO | 99/57246 | 11/1999 |
| WO | 00/03000 | 1/2000 |
| WO | 01/11021 | 2/2001 |
| WO | 01/14529 | 3/2001 |
| WO | 01/23527 | 4/2001 |

OTHER PUBLICATIONS

Biochrom AG; HAM's F-12 Medium Formulation Information, 1 page.
Biochrom AG; ISCOVE's Medium Formulation Information (German Version), 1 page.
Biochrom AG; RPMI 1640 Medium Formulation Information (German Version), 1 page.
Biogen IDEC MA, Inc. Opposition Brief to European Patent No. 1200561, dated Mar. 14, 2007.
Brown, M.E. et al., "Process Development for the Production of Recombinant Antibodies Using the Glutamine Synthetase (GS) System"; 1992; Cytotechnology; vol. 9; pp. 231-236.
Burger, C. et al., "An Integrated Strategy for the Process Development of a Recombinant Antibody-Cytokine Fusion Protein Expressed in BHK Cells"; 1999; Appl. Microbiol. Biotechnol.; vol. 52; pp. 345-353.
Cambrex; Classical Media Formulations, specifically MEM Product Information, 1 page.
Campina Nederland Holding B.V. Opposition Brief to European Patent No. 1220893, dated Mar. 21, 2007.
Cartier, M. and Stanners, C.P., "Stable, High-Level Expression of a Carcinoembryonic Antigen-encoding cDNA After Transfection and Amplification with eh Dominant and Selectable Asparagine Synthetase Marker"; 1990; Gene; col. 95; pp. 223-230.
Cole, E.S. et al., "Recombinant Human Thyroid Stimulating Hormone: Development of a Biotechnology Product for Detection of Metastatic Lesions of Thyroid Carcinoma"; Sep. 1993; Biotechnology; vol. 11; pp. 1014-1024.
Cruz, H.J. et al., "Adaptation of BHK Cells Producing a Recombinant Protein to Serum-Free Media and Protein-Free Medium"; 1998; Cytotechnology; vol. 26; pp. 59-64.
Dawson, M.E., "The significance of endotoxin to cell culture and biotechnology," Mar. 1998, LAL Update, vol. 16, No. 1, 4 pages.
Declaration of Dr. Ricardo Matanguihan in support of Maxygen, Inc. Opposition Brief to European Patent No. 1220893, dated Mar. 20, 2007 (including Annexes A and B).
Declaration of Dr. Ruediger Heidemann in support of Maxygen, Inc. Opposition Brief to European Patent No. 1220893, dated Mar. 20, 2007 (including Annexes A-F).
Declaration of Anthonie Kunst for European Patent No. 1220893 dated Nov. 27, 2008 in relation to the composition of the soy hydrolysate HyPep 1510.
Deltown Specialties; Peptone Selection Guide for Diagnostic and Fermentation Nutrients, 1994, 4 pages.
Donaldson, M.S. and Sculer M.L., "Low-Cost Serum-Free Medium for the BTI-Tn5B1-4 Insect Cell Line"; 1998; Biotechnol. Prog.; vol. 14; pp. 573-579.
Doyle, A. et al. eds., "Cloning," Part 4D Module 4D1 in Cell & Tissue Culture: Laboratory Procedures; 1998; John Wiley & Sons; London; Cloning Techniques (Non-hybridoma Related); pp. 4D:1.1-4D:1.9.
Eagle, H., "Amino Acid Metabolism in Mammalian Cell Cultures"; Aug. 21, 1939; Science; vol. 130; pp. 432-437.
Extract from Hauser, H. and Wagner, R. eds.; Mammalian Cell Biotechnology in Protein Production; 1997; Walter de Gruyter, Berlin; pp. 33-137.
Extract from Quest International; "Sheffield Series" Products Catalogue, 13 pages.
Farrell, P.J. et al., "High-Level Expression of Secreted Glycoproteins in Transformed Lepidopteran Insect Cells Using a Novel Expression Vector"; Dec. 20, 1998; Biotechnology and Bioengineering; vol. 60(6); pp. 656-663.
Faure, T. et al., "Stable Expression of Coagulation Factors FVIII and Fix in Recombinant Chinese Hamster Ovary Cells"; 1989; Meeting Info. 9th General Meeting of the European Society for Animal Cell Technology; Knokke (Belgium); 1988; pp. 481-488.
F. Hoffmann-LaRoche AG Opposition Brief to European Patent No. 1200561, dated Mar. 13, 2007.
F. Hoffmann-La Roche AG Opposition Brief to European Patent No. 1220893, dated Mar. 27, 2007.
Field, R.P. et al., "Production of a Chimeric Antibody for Tumour Imaging and Therapy From Chinese Hamster Ovary (CHO) and Myeloma Cells"; May 1990; Proceedings of the 10th ESACT Meeting; pp. 742-744.
Fischer et al., "Structural Analysis of Recombinant von Willebrand Factor: Identification of Hetero- and Homo-Dimers"; 1994; FEBS Letters; vol. 351; pp. 345-348.
Fischer, B. et al., "Comparison of N-Glycan Pattern of Recombinant Human Coagulation Factors II and IX Expressed in Chinese Hamster Ovary (CHO) and African Green Monkey (Vero) Cells"; 1996; J. Thrombos. and Trombolys. ; vol. 3; pp. 57-62.
Fischer, B.E. et al., "Biochemical and Functional Characterization of Recombinant von Willebrand Factor Produced on a Large Scale"; 1997; CMLS; vol. 53; pp. 943-950.
Fischer, B.E. et al., "Structural Analysis of Recombinant von Willebrand Factor Produced at Industrial Scale Fermentation of Transformed CHO Cells Co-expressing Recombinant Furin"; 1995; FEBS Letters; vol. 375; pp. 259-262.
Franek, F. et al., "Plant Protein Hydrolysates: Preparation of Defined Peptide Fractions Promoting Growth and Production in Animal Cells Cultures"; 2000; Biotechnol. Prog.; vol. 16; No. 5; pp. 688-692.
Freshney, R.I., "The Culture Environment: Substrate, Gas Phase, Medium, and Temperature"; Chapter 7 in Culture of Animal Cells a Manual of Basic Technique, 2nd Edition; 1987; pp. 57-84.
Friedman, J.S. et al., "High Expression in Mammalian Cells Without Amplication"; Apr. 1989; Biotechnology; vol. 7; pp. 359-362.

(56) References Cited

OTHER PUBLICATIONS

Gandor, C., "Amplification and Expression of Recombinant Genes in Serum-Independent Chinese Hamster Ovary Cells"; 1995; FEBS Letters; vol. 377; pp. 290-294.
Gorfein, S.F. et al., "Recombinant Protein Production by CHO Cells Cultured in a Chemically Defined Medium"; 1996; presented at JAACT, Yokohama: Japan; 16 pages.
Haldankar, R. et al., "Stable Production of a Human Growth Hormone Antagonist From CHO Cells Adapted to Serum-Free Suspension Culture"; 1999; Biotechnol. Prog.; vol. 15(3); pp. 336-346.
Ham, R.G., "Clonal Growth of Mammalian Cells in a Chemically Defined, Synthetic Medium"; 1965; PNAS; vol. 53; pp. 288-293.
Harant, H. et al., "Two-Dimensional Electrophoresis as a Tool for Control of Quality and Consistency in Production Systems Using Animal Cells"; 1992; Cytotechnology; vol. 8; pp. 119-127.
Harrison, S. et al., "The Manufacturing Process for Recombinant Factor IX"; Apr. 1998; Seminars in Hematology; vol. 35(2), Suppl. 2; pp. 4-10.
Hassell, T. et al., "Stability of Production of Recombinant Antibodies from Glutamine Synthetase Amplified CHO and NS0 Cell Lines"; 1992; Animal Cell Technology: Developments, Processes and Products, 11th ESACT Meeting; pp. 42-47.
Heidemann, R. et al., "The Use of Peptones as Medium Additives for High-Density Perfusion Cultures of Animal Cells"; Poster Presented at the 16th ESACT Meeting, Apr. 25-29, 1999, Lugano, Switzerland; 3 pages.
Heidemann, R. et al., "The Use of Peptones as Medium Additives for the Production of a Recombinant Therapeutic Protein in High Density Perfusion Cultures of Mammalian Cells"; 2000; Cytotechnology; vol. 32; pp. 157-167.
Hsieh, C.M. et al., "The Effect of Soy Protein Hydrolyzates on Fermentation by *Lactobacillus amylovorus*"; 1999; Process Biochemistry; vol. 34; pp. 173-179.
Inoue, Y. et al., "Production of Recombinant Human Monoclonal Antibody Using ras-Amplified BHK-21 Cells in a Protein-free Medium"; 1996; Biosci. Biotech. Biochem.; vol. 60(5); pp. 811-817.
Ito, Y. et al., "Protein-Free Cell Culture on an Artificial Substrate with Covalently Immobilized Insulin"; 1996; Proc. Natl. Acad. Sci. USA; vol. 93; pp. 3598-3601.
Jan, D.C-H. et al., "Peptone a Low-Cost Growth-Promoting Nutrient for Intensive Animal Cell Culture"; Cytotechnology; vol. 16; pp. 17-26, 1999.
Jin, B.R. et al., "Production Kinetics and Stability of a Transfectoma Cell Line Secreting Murine/Human Chimeric Antibody"; 1993; Mol. Cells; vol. 3; pp. 233-237.
Kadouri, A. et al., "Dynamic Changes in Cytokine Secretion by Stromal Cells During Prolonged Maintenance Under Protein-Free Conditions"; 1992; International Journal of Cell Cloning; vol. 10; pp. 299-308.
Katinger, H. et al., "Long-Term Stability of Continuously Perfused Animal Cells Immobilized on Novel Macroporous Microcarriers"; 1996; Adv. Molecul. Cell Biol.; vol. 15A; pp. 193-207.
Katsuta, H. and Takaoka, T., "Amino Acid Requirements of a Substrain of StrainL Cells (Mouse Fibroblasts) in Protein-Free Chemically Defined Synthetic Media"; 1960; Japan J. Exp. Med.; vol. 30; pp. 235-259.
Katsuta, H. et al., "Effects of Polyamines on the Proliferation of Mammalian Cells in Tissue Culture"; 1975; The Japanese Journal of Experimental Medicine; vol. 45; No. 5; pp. 345-354.
Kaufman, K. et al., "Effect of von Willebrand Factor Coexpression on the Synthesis and Secretion of Factor VIII in Chinese Hamster Ovary Cells"; 1989; Molecul. Cellul. Biol.; vol. 9(3); pp. 1233-1242.
Keay, L., "Autoclavable Low Cost Serum-Free Culture Media, the Growth of L Cells and BHK Cells on Peptones"; 1975; Biotechnology and Bioengineering; vol. XVII; pp. 745-764.
Keay, L., "Autoclavable Low Cost Serum-Free Cell Culture Media: the Growth of Established Cell Lines and Production of Viruses"; 1976; Biotechnology and Bioengineering; vol. XVIII; pp. 363-382.
Keen, M.J. and Rapson, N.T., "Development of a Serum-Free Culture Medium for the Large Scale Production of Recombinant Protein From a Chinese Hamster Ovary Cell Line"; 1995; Cytotechnology; vol. 17; pp. 153-163.
Kerry Bio-Science; Pharma Ingredients Site for Hydrolysates, 4 pages.
Keny Ingredients (UK) Limited Opposition Brief to European Patent No. 1220893, dated Mar. 21, 2007.
Kim, N.S. et al., "Clonal Variability Within Dihydrofolate Reductase-Mediated Gene Amplified Chinese Hamster Ovary Cells: Stability in the Absence of Selective Pressure"; Dec. 20, 1998; Biotechnology and Bioengineering; vol. 60(6); pp. 679-688.
Kim, S.J. et al., "Characterization of Chimeric Antibody Producing CHO Cells in the Course of Dihydrofolate Reductase-Mediated Gene Amplification and Their Stability in the Absence of Selective Pressure"; Apr. 5, 1998; Biotechnology and Bioengineering; vol. 58(1); pp. 73-84.
Kwon, M.S. et al., "Use of Plant-Derived Protein Hydrolysates for Enhancing Growth of Bombyx mori (silkworm) Insect Cells in Suspension Culture"; 2005; Biotechnology and Applied Biochemistry; vol. 42, No. 1; pp. 1-7.
Lee, K.H. et al., "Deregulated Expression of Cloned Transcription Factor E2F-1 in Chinese Hamster Ovary Cells Shifts Protein Patterns and Activates Growth in Protein-Free Medium"; 1996; Biotechnol. Bioeng.; vol. 50; pp. 273-279.
Luchette, C. et al., "Isolation and Characterization of a CHO Cell Line Express rhFSH in Low Protein and Protein-Free Media"; 1997; Animal Cell Technology; pp. 669-674.
Maxygen, Inc. Opposition Brief to European Patent No. 1200561, dated Mar. 14, 2007.
Maxygen, Inc. Opposition Brief to European Patent No. 1220893, dated Mar. 20, 2007.
Merck Serono International S.A. Opposition Brief to European Patent No. 1200561, dated Mar. 12, 2007.
Merck Serono International S.A. Opposition Brief to European Patent No. 1220893, dated Mar. 20, 2007.
Merten, O.-W. et al., "Production of Influenza Virus in Serum-Free Mammalian Cell Cultures"; 1999; Dev. Biol. Stand.; vol. 98; pp. 23-37.
Merten, O.-W. et al., "The New Medium MDSS2N, Free of Any Animal Protein Supports Cell Growth and Production of Various Viruses"; 1999; Cytotechnology; vol. 30; pp. 191-201.
Merten, O.-W., "Safety Issues of Animal Products Used in Serum-Free Media"; 1999; Dev. Biol. Stand.; vol. 99; pp. 167-180.
Minutes of the Oral Proceedings to EP 99 939 251.7, 4 pages.
Miyaji, H. et al., "Efficient Expression of Human Beta-interferon in Namalwa KJM-1 Cells Adapted to Serum-free Medium by a dhfr Gene Coamplification Method"; 1990; Cytotechnology; vol. 4; pp. 173-180.
Miyati, H. et al., "Expression of Human Beta-interferon in Namalwa KJM-1 Which Was Adapted to Serum-free Medium"; 1990; Cytotechnology; vol. 37; pp. 133-140.
Motz, M. et al., "Expression of the Epstein-Barr Virus Major Membrane Proteins in Chinese Hamster Ovary Cells"; 1986; Gene; vol. 44(2-3); pp. 353-359; Abstract, 1 page.
Murhamivier, D.W. and Gooche, C.F., "Structural Features of Nonionic Polyglycol Polymer Molecules Responsible for the Protective Effect in Sparged Animal Cell Bioreactors"; 1990; Biotechnol. Prog.; vol. 6; pp. 142-146.
Nilsson, K. et al., "Microcarrier Culture of Recombinant Chinese Hamster Ovary Cells for Production of Human Immune Interferon and Human Tissue-Type Plasminogen Activator"; 1988; Appl. Microbiol. Biotechnol.; vol. 27; pp. 366-371.
Novartis AG Opposition Brief to European Patent No. 1200561, dated Mar. 14, 2007.
Novartis AG Opposition Brief to European Patent No. 1220893, dated Mar. 21, 2007.
Novo Nordisk A/S Opposition Brief to European Patent No. 1200561, dated Mar. 14, 2007.

(56) References Cited

OTHER PUBLICATIONS

Novo Nordisk A/S Opposition Brief to European Patent No. 1220893, dated Mar. 21, 2007.
N.V. Organon Opposition Brief to European Patent No. 1200561, dated Mar. 14, 2007.
Nyberg, G.B. et al., "Metabolism of Peptide Amino Acids by Chinese Hamster Ovary Cells Grown in a Complex Medium"; Feb. 5, 1999; Biotechnology and Bioengineering; vol. 62(3); pp. 324-335.
Ochiai, M. et al., "Endotoxin Content in *Haemophilus influenzae* Type b Vaccine"; 2004; Jpn J. Infect. Dis.; vol. 57; pp. 58-59.
Ogata, M. et at, "High-Level Expression of Recombinant Human Soluble Thrombomodulin in Serum-Free Medium by CHO-K1 Cells"; 1993; Appl. Microbiol. Biotechnol.; vol. 38; pp. 520-525.
Page from the Quest International Technical Manual on Hydrolysates, 1988.
Pak, S.C.O. et al., "Super-CHO—A Cell Line Capable of Autocrine Growth Under Fully Defined Protein-Free Conditions"; 1996; Cytotechnology; vol. 22; pp. 139-146.
Paterson, T. et al., "Approaches to Maximizing Stable Expression of αl-Antitrypsin in Transformed CHO Cells"; 1994; Appl. Microbiol. Biotechnol.; vol. 40; pp. 691-698.
Product Information "Bacto™" TC Yeastolate TC Yeastolate, UF, 2 pages.
Pu, H. et at, "Rapid Establishment of High-Producing Cell Lines Using Dicistronic Vectors with Glutamine Synthetase as the Selection Marker"; 1998; Molecular Biotechnology; vol. 10; pp. 17-25.
Qi, Y.M. et al., "Evaluation of a Simple Protein Free Medium That Supports High Levels of Monoclonal Antibody Production"; 1996; Cytotechnology; vol. 21; pp. 95-109.
Quest International; Bioproducts Group HY-SOY 2 ®, Product Information, 1995, 1 page.
Quest International; "Protein Derived Peptide Mixtures can Effectively Replace Serum, Glutamine and Other Free Amino Acids in Cell Culture Media"; Nov. 1998; Research Disclosure; pp. 1474-1476.
Quest International; Bioproducts Group HY-SOY®, Product Information, 1995, 1 page.
Quest International; Bioproducts Group HY-SOY®, Product Information, 1998, 2 pages.
Quest International; HyPep® 1510 (IPL:5Z10493) Product Information, 2 pages.
Quest International; Pharma Ingredients Site with Product Information for HyPep® 1510 and Hy-Soy®, 11 pages.
Quest International; Product Information; www.sheffield-products.com; accessed on Nov. 18, 2003; 14 pages.
Rasmussen, B. et al., "Isolation, Characterization and Recombinant Protein Expression in Veggie-CHO: A Serum-Free CHO Host Cell Line"; 1998; Cytotechnology; vol. 28; pp. 31-42.
Reiter, M. et al., "Flow Cytometry and Two-Dimensional Electrophoresis (2-DE) for System Evaluation of Long Term Continuous Perused Animal Cell Cultures in Macroporous Beads"; 1992; Cytotechnology; vol. 9; pp. 247-253.
Renner, W.A. et al., "Recombinant Cyclin E Expression Activates Proliferation andObvates Surface Attachment of Chinese Hamster Ovary (CHO) Cells in Protein-Free Medium"; Aug. 1995; Biotechnology and Bioengineering; vol. 47; pp. 476-482.
Ryll, T. et al., "Production of Recombinant Human Interleukin-2 with BHK Cells in a Hollow Fibre and a Stirred Tank Reactor with Protein-Free Medium"; 1990; Journal of Biotechnology; vol. 14; pp. 377-392.
SAFC Biosciences™; Dulbecco's Modified Eagle's Medium/Ham's Nutrient Mixture F12 Product Information, 2006, 2 pages.
SAFC Biosciences™; RPMI 1640 Medium Modified Product Information, 2006, 2 pages.
Scharfenberg, K. and Wagner, R., "A Reliable Strategy for the Achievement of Cell Lines Growing in Protein-Free Medium"; 1995; Animal Cell Technology: Developments towards the 21st Century; pp. 619-623.
Schlaeger, E.J., "The Protein Hydrolystate, Primatone RL, is a Cost-Effective Multiple Growth Promoter of Mammalian Cell Culture in Serum-Containing and Serum-Free Media and Displays Anti-apoptosis Properties"; 1996; Journal of Immunological Methods; vol. 194; pp. 191-199.
Schlokat, U. et al., "Herstellung and Charakterisierung von rekombinantem vonWillebrand-Faktor zur Therapeutischen Anwendyng"; 1995; 26th Hämophilie-Symposium Hamburg; pp. 147-158.
Schlokat, U. et al., "Production of Highly Homogeneous and Structurally Intact Recombinant von Willebrand Factor Multimers by Furin-Mediated Propeptide Removal in vitro"; 1996; Biotechnol. Appl. Biochem.; vol. 24; pp. 257-267.
Schneider, Y-J, "Optimisation of Hybridoma Cell Growth and Monoclonal Antibody Secretion in a Chemically Defined, Serum- and Protein-Free Culture Medium"; 1989; Journal of Immunological Methods; vol. 116; pp. 65-77.
Sigma®; Biochemicals Organic Compounds Diagnostic Reagents Catalogue, 1995, 6 pages.
Sigma-Aldrich; DME/Nutrient Mixture F12 Ham Product Information, 8 pages.
Sigma-Aldrich; Dulbecco's Modified Eagle's Medium (DME)/Ham's Nutrient Mixture F-12, Product Information, 2 pages.
Sigma-Aldrich; IPL-41 Insect Medium Product Information, 1 pages.
Sigma-Aldrich; Minimum Essential Medium Eagle (MEM), Product Information, 6 pages.
Sigma-Aldrich; Minimum Essential Medium Eagle, Joklik Modification, Specification Sheet, 1 page.
Sigma-Aldrich; P1265 N-Z Soy Peptone Product Detail, 1 page.
Sigma-Aldrich; P6463 Peptone Hy-Soy® T Product Detail, 1 page.
Sigma-Aldrich Co. Opposition Brief to European Patent No. 1220893, dated Mar. 21, 2007.
Sinacore, M.S. et al., "CHO DUKX Cell Lineages Preadapted to Growth in Serum-Free Suspension Culture Enable Rapid Development of Cell Culture Processes for the Manufacture of Recombinant Proteins"; 1996; Biotechnol. Bioeng.; vol. 52; pp. 518-528.
Stoll, T.S. et al. "Effects of Culture Conditions on the Production and Quality of Monoclonal IgA"; Aug. 15, 1997; Enzyme and Microbial Technology; vol. 21; pp. 203-211.
Sunstrom, N-A. et al., "Recombinant Insulin=like Growth Factor-I (IGF-I) Production in Super-CHO Results in the Expression of IGF-I Receptor and IGF Binding Protein 3"; 1998; Cytotechnology; vol. 28; pp. 91-99.
Takahashi, M. et at, "Production of Murine Monoclonal Antibodies in Protein Free Medium"; 1997; Animal Cell Technology: Basic & Applied Aspects; vol. 8; pp. 167-171.
Taylor, W.G. et al., "Studies on a Serum Substitute for Mammalian Cells in Culture. I. Biological Efficacy of Whole and Fractionated Peptone Dialysate (36086)"; 1972; Proc. Soc. Exp. Biol. Med.; vol. 139; pp. 96-99.
Tecce, M.F. and Terrana, B., "High Yield and High-Degree Purification of Human α-Fetoprotein Produced by Adaptation of the Human Hepatoma Cell Line HEP G2 in a Serum-Free Medium"; 1988; Analytical Biochemistry; vol. 169; pp. 306-311.
Teige, M. et al., "Problems with Serum-Free Production of Antithrombin III Regarding Proteolytic Activity and Product Quality"; 1994; Journal of Biotechnology; vol. 34; pp. 101-105.
Werner et al., "Safety and economic aspects of continuous mammalian cell culture," J. Biotechnol., 1992, 22:51-68.
Wyeth Opposition Brief to European Patent No. 1200561, dated Mar. 14, 2007.
Yamauchi, T. et al., "Production of Human Antithrombin-III in a Serum-Free Culture of CHO Cells"; 1992; Biosci. Biotech. Biochem; vol. 56(4); pp. 600-604.
Yin, Z. et al., "Sensitivity of 3T3 Cells to Low Serum Concentration and the Association Problems of Serum Withdrawal"; 1994; Cell Biology International; vol. 18(1); pp. 39-46.
Zang, M. et al., "Production of Recombinant Proteins in Chinese Hamster Ovary Cells Using a Protein-Free Cell Culture Medium"; 1995; Biotechnology; vol. 13; pp. 389-392.
Zang-Gandor, M.O.; "Improved Transfection of CHO Cells Using Endotoxin-Free Plasmid DNA"; Quiagen News; 1997; vol. 4; pp. 1, 16-18.

MEDIUM FOR THE PROTEIN-FREE AND SERUM-FREE CULTIVATION OF CELLS

CROSS-REFERENCE TO RELATED APPLICATIONS

This application is a continuation of U.S. application Ser. No. 14/231,221, filed Mar. 31, 2014, which is a continuation of U.S. application Ser. No. 13/198,476, filed Aug. 4, 2011, Now U.S. Pat. No. 8,722,406, which is a continuation of U.S. application Ser. No. 11/841,915, filed Aug. 20, 2007, now U.S. Pat. No. 8,021,881, which is a continuation of U.S. application Ser. No. 10/405,794, filed Apr. 1, 2003, now abandoned, which is a continuation of U.S. application Ser. No. 09/672,240, filed Sep. 28, 2000, now abandoned, which claims priority from Austrian Application No. A1659/99, filed Sep. 28, 1999, the disclosures of each of which are herein incorporated by reference in their entireties for all purposes.

The present invention pertains to a medium for the protein-free and serum-free cultivation of cells.

BACKGROUND OF THE INVENTION

The cultivation of cells, especially eukaryotic cells or mammalian cells, constantly calls for the use of special culture media that make available to the cells the nutrient substances and growth substances that are required for efficient growth and for the production of the proteins that are desired. As a rule, serum or compounds that are derived from serum (e.g. bovine serum) are used as a component of the medium in this regard.

However, in the case of the use of serum or protein additives that are derived from human or animal sources in cell cultures, numerous problems exist, especially if the starting material for the preparation of a medicinal agent that is to be administered to humans is made available via the cell culture.

In the case of such serum preparations, therefore, the composition and quality already vary from batch to batch just because of the dissimilarity of the donor organisms for such preparations. This represents a considerable problem, especially for the standardization of cell production and in establishing standard growth conditions for such cells. However, intensive and constant quality control of the serum material that is used is required in every case. However, this is extremely time-consuming and cost intensive, especially in the case of such complex compositions as serum.

Moreover, such complex preparations contain a plurality of proteins that can act in a disruptive manner, especially within the context of the purification process for the recombinant protein that is to be recovered from the cell culture. This applies particularly to those proteins that are homologous with or similar to the protein that is to be recovered.

Naturally, these problems are especially acute in the case of the recombinant recovery of serum proteins because the biogenic pendant in the medium that is used (e.g., bovine protein) can be removed reliably within the context of purification only via quite specific differential purification (e.g., with antibodies that are directed specifically only against the recombinant protein but not against the bovine protein (Bjorck, L., J. Immunol., 1988, Vol. 140, pp. 1194-1197; Nilson et al., J. Immunol Meth., 1993, 164, pp. 33-40).

Another issue in the use of serum or compounds which are derived from serum in the culture medium is the possibility of contamination by mycoplasma, viruses BSE agents, or disease-inducing agents that are as yet unknown.

The addition of serum components in order to guarantee adequate adhesion of the cells to their surfaces and to guarantee adequate production of the desired substances from the cells has, apart from a few exceptions, been previously regarded as indispensable precisely for the cultivation of cells on solid surfaces. Thus with the method that is described in WO 91/09935, for example, it has been possible to achieve a process for the serum-free and protein-free cultivation of the FSME virus/virus antigen by means of the serum-free and protein-free cultivation of surface-dependent permanent cells, preferably vero cells (see WO 96/15231). However these are not recombinant cells but, rather, host cells that are used for the production of virus antigen in a lytic process.

In contrast to this, the cells that are used preeminently for a recombinant preparation, for example CHO cells, are capable of adhering only to a limited extent. Thus, CHO cells that have been bred by conventional methods bind to both smooth and porous microcarriers only under serum-containing conditions (see U.S. Pat. No. 4,973,616; Cytotechnology 9 (1992), 247-253). However, if such cells are bred under serum-free conditions, they lose this property and do not adhere to smooth carriers, or they become detached with ease therefrom if other adhesion-promoting additions, such as e.g., fibronectin, insulin or transferrin, have not been provided in the medium. However these are also proteins that are derived from serum.

Alternatively to this, the cells can be bred using the suspension culture technique as well as e.g., using the batch process or using a continuous culture technique. Cultivation preferably takes place using the chemostat process (Ozturk S. S. et al., 1996, Abstr. Pap. Am. Chem. Soc., BIOT 164, Payne G. F. et al., in "Large Scale Cell Culture Technology," 1987, ed. Lydersen B. K., Hauser publishers; pp. 206-212). Kattinger H. et al (Advances Mol. Cell. Biology, 1996, 15A, 193-207) describe the long term cultivation of cells in protein-free medium, but these cells must be cultivated on carriers and do not leave alternatives as continuous culture techniques. It is stated that these cells only show long term stability when adhered to the surface of carriers because of reduced growth and, as a consequence, reduced demand for growth factors.

In addition, attempts have been made on several occasions in the prior art to adapt cells to a protein-free medium starting from serum-containing conditions. However, in the case of such adaptation, it has been found repeatedly that, compared to serum-containing conditions, the yield of expressed protein and the productivity of the recombinant cells are markedly reduced in the protein-free medium following adaptation (Appl. Microbiol. Biotechnol. 40 (1994), 691-658)

It has also been found that, in the case of a high cell density, the production of recombinant proteins is considerably restricted on occasions. During attempts to adapt the cells to protein-free or serum-free media, instability with reduced growth of the cells, which are used, is also found repeatedly so that cells with reduced expression are produced, or even nonproducing cells are produced, whereby these have a growth advantage, relative to the producing cells, in protein-free and serum-free media, and this leads to the fact that these overgrow the producing cells and then, finally, the entire culture now generates very low product yields.

SUMMARY OF THE INVENTION

The present invention has therefore an objective of improving the possibilities for the protein-free and serum-free cultivation of recombinant cells and of making agents and processes available with which recombinant cells can be cultivated efficiently in a serum-free or protein-free manner. Moreover, it should then be possible not only to culture surface-dependent cells, but also to use the suspension culture technique, whereby instability in the productivity of the cells is required to be repressed as much as possible.

A further objective of the present invention additionally is to efficiently increase the production of recombinant cells.

Finally, in accordance with the invention, the adaptation of recombinant cells to serum-free and protein-free media is required to be improved and configured more efficiently.

In accordance with the invention, these tasks are accomplished by means of a medium for the protein-free and serum-free cultivation of cells, especially mammalian cells, characterized by the feature that the medium contains a proportion of soy hydrolysate.

Surprisingly, it has been possible to show that the objectives, which were defined above, can be achieved by cultivating cells in a medium that contains soy hydrolysate, without having to tolerate the disadvantages of serum-free cultivation which are described in the prior art. In contrast to other hydrolysates which are known in the prior art, such as for example wheat hydrolysates, rice hydrolysates or yeast hydrolysates, it has been found that only soy hydrolysate mediates the properties in accordance with the invention and leads, for example, to a significantly increased yield of the recombinant target protein. When dealing with these terms, either the term soy hydrolysate or the term soy peptone can be used without having different meanings.

DETAILED DESCRIPTION OF THE INVENTION

Figure 1A:
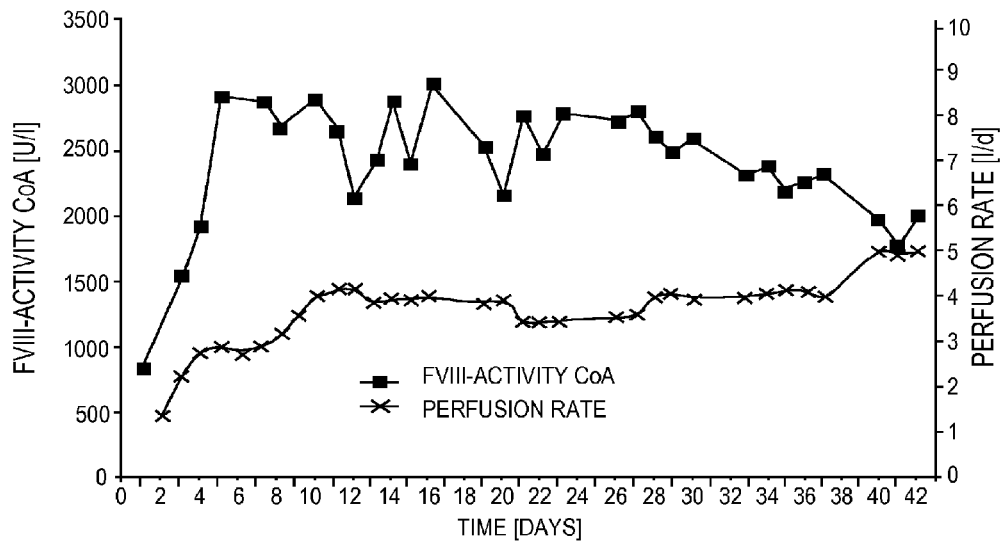
FIGS. 1A-1B show the results of the cultivation of a rFVIII-CHO cell clone in a 10-L perfusion bioreactor:
a) Factor VIII activity (milliunits/mL) and the perfusion rate (1-5/day) over a period of 42 days;
b) volumetric productivity (units of Factor VIII/L/day) in the perfusion bioreactor.

The medium in accordance with the invention preferably contains soy hydrolysate in a quantity of more than 10 wt % based on the total dry weight of the medium. As a rule, the soy hydrolysate in the medium is provided in a quantity of 4-40%.

The choice of specific soy hydrolysate is not critical in accordance with the invention. A plurality of soy preparations, which are to be found on the market, can be used in accordance with the invention, e.g., peptones from soy flour, digested enzymatically (e.g., by papain), with a pH value between 6.5 and 7.5 and a total nitrogen content between 9% and 9.7% and an ash content between 8 and 15%. These are peptones from soybeans in the form in which they are generally used for cell culture by the expert in the field.

In accordance with a preferred form of embodiment, use is made of a purified preparation of a soy hydrolysate or a crude fraction thereof in the medium in accordance with the invention. Impurities which could interfere with efficient cultivation are preferably eliminated during this purification, or the precision of the hydrolysate is improved, e.g., in regard to the molecular weight.

In accordance with the invention, the provision of an ultrafiltration step has proven to be especially valuable in practice during this purification; because of this, the use of ultrafiltered soy hydrolysate is especially preferred in the medium in accordance with the invention.

Ultrafiltration can take place in accordance with the process as described comprehensively in the prior art, e.g., with use being made of membrane filters with a defined cut-off limit.

The purification of the ultrafiltered soy peptone can take place by means of gel chromatography, e.g., by means of Sephadex chromatography, for example, with Sephadex G25 or Sephadex G10 or equivalent materials, ion-exchange chromatography, affinity chromatography, size exclusion chromatography or "reversed-phase" chromatography. These are processes from the prior art with which the expert in the field is familiar. Using this method, those fractions can be selected which contain soy hydrolysate of defined molecular weight, i.e. ≤1000 Dalton, preferably ≤500 Dalton, more preferably ≤350 Dalton. Therefore the invention also comprises a process for producing a serum-free and protein-free cell culture medium, comprising obtaining a soy hydrolysate, ultrafiltering said soy hydrolysate using an ultrafiltration process, purifying said soy hydrolysate fraction using size exclusion chromatography and selecting the soy hydrolysate fractions consisting of soy hydrolysate having a molecular weight ≤1000 Dalton, preferably ≤500 Dalton, more preferably ≤350 Dalton.

An especially advantageous soy hydrolysate is characterized by the feature that it has a free amino acids content of between 10.3 and 15.6% or, preferably, between 12 and 13.5%, a total nitrogen content of between 7.6 and 11.4% or, preferably, between 8.7 and 9.5% and an endotoxin content of <500 U/g and whereby at least 40% or, preferably, at least 50% or, especially preferably, at least 55% thereof has a molecular weight of 200-500 daltons and at least 10% or, preferably, 15% thereof has a molecular weight of 500-1000 daltons. Most preferably, at least 90% of the soy hydrolysate is of a molecular weight of ≤500 Daltons. Such a soy hydrolysate is especially well suited to the industrial production of recombinant proteins since, because of its special features, it can be standardized especially easily and it is usable in routine processes.

In addition to soy hydrolysate, the medium in accordance with the invention can also contain synthetic media in a way that is known as such, such as e.g., DMEM/HAM's F12, Medium 199 or RPMI, that are adequately known from the literature.

Moreover, the medium in accordance with the invention also preferably contains amino acids, preferably those selected from the group comprising L-asparagine, L-cysteine, L-cystine, L-proline, L-tryptophan, L-glutamine, or mixtures thereof.

The following amino acids are also preferably added to the medium in accordance with the invention: L-asparagine (in a quantity of 0.001-1 g/L of medium, preferably 0.1-0.05 g/L, especially preferably 0.015-0.03 g/L); L-cysteine (0.001-1 g/L, preferably 0.005-0.05 g/L, especially preferably 0.01-0.03 g/L); L-cystine (0.001-1 g/L, preferably 0.01-0.05 g/L, especially preferably 0.015-0.03 g/L); L-proline (0.001-1.5 g/L, preferably 0.01-0.07 g/L, especially preferably 0.02-0.05 g/L); L-tryptophan (0.001-1 g/L, preferably 0.01-0.05 g/L, especially preferably 0.015-0.03 g/L); and L-glutamine (0.05-1 g/L, preferably 0.1-1 g/L).

The amino acids designated above can be added to the medium in accordance with the invention either individually or in combination. The combined addition of an amino acid mixture, which contains all of the above-mentioned amino acids, is especially preferred.

A serum-free and protein-free medium is used in a special form of embodiment, whereby this medium additionally contains a combination of the above-mentioned amino acid mixture and purified ultrafiltered soy peptone.

Surprisingly, for example, it has been found that in order to inactivate viruses or other pathogens, the medium can be heated, without negative effects, for approximately 5-20 min or, preferably, 15 min at 70-95° C. or, preferably, 85-95° C.

In accordance with the invention, a known synthetic medium can be used in combination with the soy hydrolysate. Conventional synthetic media can contain inorganic salts, amino acids, vitamins, a source of carbohydrates and water. For example, use can be made of DMEM/HAM's F12 medium. The concentration of soy extract in the medium can preferably be between 0.1 and 100 g/L, especially preferably, 1 and 5 g/L. In accordance with an especially preferred form of embodiment, soy peptone can be used which has been standardized in regard to its molecular weight. The molecular weight of the soy peptone preferably is less than 50 kD, especially preferably less than 10 kD, most preferably, less than 1 kD.

The addition of ultrafiltered soy peptone has proven to be especially advantageous for the productivity of the recombinant cell lines, whereby the average molecular weight of the soy peptone is 350 daltons (Quest Company). This is a soy isolate with a total nitrogen content of approximately 9.5% and a free amino acid content of approximately 13%.

The use of purified, ultrafiltered soy peptone with a molecular weight of ≤1,000 daltons, preferably ≤500 daltons, especially preferably ≤350 daltons is especially preferred.

The medium in accordance with the invention also preferably contains auxiliary substances, such as e.g., buffer substances, oxidation stabilizers, stabilizers to counteract mechanical stress, or protease inhibitors.

Use is especially made of a medium with the following composition: synthetic minimal medium (1-25 g/L), soy peptone (0.5-50 g/L), L-glutamine (0.05-1 g/L), $NaHCO_3$ (0.1-10 g/L), ascorbic acid (0.0005-0.05 g/L), ethanolamine (0.0005-0.05 g/L) and Na selenite (1-15 µg/L).

If required, a nonionic surfactant, such as, e.g., polypropylene glycol (PLURONIC F-61, PLURONIC F-68, SYNPERONIC F-68, PLURONIC F-71 or PLURONIC F-108) can be added to the medium as a defoaming agent in accordance with the invention.

This agent is generally used in order to protect the cells from the negative effects of aeration since, without an addition of a surfactant, ascending and bursting air bubbles can lead to damage of those cells that are located on the surface of these air bubbles ("sparging") (Murhammer and Goochee, 1990, Biotechnol. Prog. 6:142-148).

The quantity of nonionic surfactant can be between 0.05 and 10 g/L. Preferably, the smallest possible amount is between 0.1 and 5 g/L. In addition, the medium in accordance with the invention can also contain cyclodextrin or a derivative thereof.

The serum-free and protein-free medium of the present invention preferably contains a protease inhibitor, such as a serine protease inhibitor, which is suitable for tissue culture and is of synthetic or plant origin.

Cells that have already been adapted are preferably used as the cells for cultivation in the medium in accordance with the invention, i.e., cells that have already adapted to growth in the protein-free and serum-free media. It has been found that not only can increased yields be achieved with such preadapted cells, but their stability for serum-free and protein-free cultivation is also clearly improved by the use of the medium in accordance with the invention.

However, recombinant cell clones have proven to be especially valuable in accordance with the invention, whereby these are stable from the outset for at least 40 generations and, preferably, at least 50 generations in serum-free and protein-free media, and express recombinant products.

Such cell clones are obtainable from a cell culture that is obtained following the cultivation of a recombinant original cell clone on a serum-containing medium and readaptation of the cells to a serum-free and protein-free medium.

The term "original cell clone" can be understood to mean a recombinant cell clone transfectant that, after transfection of the host cells with a recombinant nucleotide sequence, expresses a recombinant product in a stable manner under laboratory conditions. The original clone is bred in a serum-containing medium in order to optimize its growth. In order to increase its productivity, the original clone is bred, optionally in the presence of a selection agent, with selection on the selection marker and/or amplification marker. For large-scale industrial production, the original cell clone is bred, under serum-containing conditions of cultivation, to a high cell density and then it is readapted to a serum-free or protein-free medium just prior to the production phase. Cultivation preferably takes place without selection pressure in this case.

The cultivation of the recombinant original cell clone can take place from the beginning in a serum-free and protein-free medium; as a result, readaptation is no longer necessary. If required, use can also be made of a selection agent in this case and selection can take place on the selection marker and/or the amplification marker. A process for this is described in EP 0 711 835, for example.

The cell culture that is obtained after readaptation to a serum-free and protein-free medium is tested for those cell clones of the cell population which produce products in a stable manner under serum-free and protein-free conditions, optionally in the absence of selection pressure. This can take place, for example, by means of immunofluorescence with marked specific antibodies which are directed against the recombinant polypeptide or protein. The cells that are identified as product producers are isolated from the cell culture and are re-bred under serum-free and protein-free conditions that are preferably equivalent to production conditions. The isolation of the cells can thereby take place by isolating the cells and testing them for product producers.

The cell culture, containing the stable cells, can be tested again for stable recombinant clones, and these are isolated from the cell culture and subcloned. The stable recombinant cell clones that are obtained under serum-free and protein-free conditions can then be bred further under serum-free and protein-free conditions.

The recombinant cell clones or the cell populations, which are prepared in this way in the medium in accordance with the invention, excel in particular by way of the feature that they are stable for at least 40 generations, preferably for at least 50 generations and, in particular, for more than 60 generations, and express a recombinant product.

An example of such a recombinant stable cell clone or cell population has been filed, in accordance with the Budapest convention, under number 98012206 with the ECACC (UK).

The cell culture, which is to be cultivated in accordance with the invention, is preferably derived from a recombinant mammalian cell. Recombinant mammalian cells can hereby be all those cells that contain sequences which code for a recombinant polypeptide or protein. All continuously growing cells, which grow either adherently or nonadherently, are encompassed in this regard. Recombinant CHO cells or BHK cells are especially preferred. Recombinant polypeptides or proteins can be blood factors, growth factors or other biomedically relevant products.

In accordance with the present invention, cell clones are preferred which contain the coding sequence for a recombinant blood factor, such as Factor II, Factor V, Factor VII, Factor VIII, Factor IX, Factor X, Factor XI, Protein S, Protein C, an activated form of one of these factors, or vWF, and that are capable of expressing these in a stable manner over several generations. Recombinant CHO cells that express vWF or a polypeptide with vWF activity, Factor VIII or a polypeptide with VIII activity, vWF and Factor VIII, Factor IX or Factor II, are especially preferred in this regard.

30 generations are required in order to start a master cell bank. At least approximately 40 generations are required in order to carry out an average batch culture on the 1000-L scale. Starting out from an individual cell clone, it is possible with the medium in accordance with the invention to prepare a "master cell bank" (MCB) and a "working cell bank" (WCB) with approximately 8-10 generations, and hence a cell culture with up to 20-25 generations under protein-free and serum-free conditions on the production scale (product on biomass) whereas, by contrast, some generations become unstable after growth on a serum-free or protein-free medium with previous cell clones and media and, as a result, a) a uniform cell culture with product producers is not possible and b} stable product productivity over an extended period of time is not possible.

However, in accordance with the invention, it was even possible, by contrast, to find increased product productivity even in comparison to the original cell clone that had been cultivated in a serum-containing medium.

In accordance with a further aspect, the present invention also pertains to a process for the cultivation of cells, especially mammalian cells, that is characterized by the feature that these cells are introduced into a medium in accordance with the invention and then are cultured in this medium.

Thus the present invention also pertains to the use of the medium in accordance with the invention for the cultivation of recombinant cells, preferably eukaryotic cells and, especially, mammalian cells. The subject of the present invention, accordingly, is also a cell culture that comprises the medium in accordance with the invention and cells, preferably eukaryotic cells, and especially mammalian cells.

The present invention further includes a process for the production of a desired protein (especially a recombinant protein) from cell culture comprising introducing cells which express such desired protein into a medium of the present invention; growing said cells in said medium and expressing said protein, thereby producing a mixture of said cells and said protein in the medium; and purifying said protein from said mixture. In this way recombinant proteins such as Factor II, Factor V, Factor VII, Factor VIII, Factor IX, Factor X, Factor XI, Protein S, Protein C, activated forms of these factors, and vWF can be produced.

The invention will be elucidated in more detail by means of the following examples below, as well as by the figures in the drawings, but it is not to be limited thereto.

EXAMPLES

Example 1

Stability of rvWF-CHO Cells After Switching from a Serum-Containing Medium to a Serum Free and Protein Free Medium.

CHO-dhfr cells were plasmid phAct-rvWF and pSV-dhfr co-transfected, and vWF-expressing clones were subcloned as described by Fischer et al. (1994, FEBS Letters 351:345-348). A working cell bank (WCB) was started from the subclones, which expressed rvWF in a stable manner, under serum-containing conditions but in the absence of MTX, and the cells were immobilized on a porous microcarrier (Cytopore●) under serum-containing conditions. Switching the cells to a serum-free and protein-free medium took place after a cell density of $2\times10^7$ cells/mL of the matrix had been reached. The cells were cultured further for several generations under serum-free and protein-free conditions. The cells were tested in a serum-free and protein-free medium at various points in time by means of immunofluorescence with labelled anti-vWF antibodies. The evaluation of the stability of the cells took place using the working cell bank prior to switching the medium, after 10 generations and after 60 generations in the serum-free and protein-free medium. Whereas the working cell bank still exhibited 100% rvWF producers, the proportion of rvWF producers declined to approximately 50% after 10 generations in the serum-free and protein-free medium. After 60 generations, more than 95% of the cells were identified as nonproducers.

Example 2

Cloning of Stable Recombinant CHO Clones.

A dilution series was prepared from the cell culture containing rvWF-CHO cells in accordance with Example 1 (this stable cell clone that was designated r-vWF-CHO F7 was filed, in accordance with the Budapest convention, with the ECACC (European Collection of Cell Cultures), Salisbury, Wiltshire SP4 OJG, UK, on Jan. 22, 1998, and acquired the deposition number 98012206) which had been cultured for 60 generations in a serum-free and protein-free medium and 0.1 cells were seeded out in each well of a microtiter plate. The cells were cultivated for approximately 3 weeks in DMEM/HAM's F12 without serum additions or protein additions and without selection pressure, and the cells were tested via immunofluorescence with labelled anti-vWF antibodies. A cell clone, which had been identified as positive, was used as the starting clone for the preparation of a seed cell bank. A master cell bank (MCB) was started from the seed cell bank in a serum-free and protein-free medium and individual ampules were put away and frozen for the further preparation of a working cell bank. A working cell bank was prepared in a serum-free and protein-free medium from an individual ampule. The cells were immobilized on porous microcarriers and cultivated further for several generations under serum-free and protein-free conditions. The cells were tested for productivity at various points in time in a serum-free and protein-free medium by means of immunofluorescence with labelled anti-vWF antibodies. The evaluation of the stability of the cells took place at the working cell bank stage and after 10 and 60 generations in a serum-free and protein-free medium. Approximately 100% of the cells were identified as positive stable clones, which express rvWF, at the working cell bank stage, after 10 generations, and 60 generations.

Example 3

Cell Specific Productivity of the Recombinant Cell Clones.

A defined number of cells was removed at defined stages during the cultivation of the recombinant cells', and these were incubated for 24 h with fresh medium. The rvWF:Risto-CoF-activity was determined in the supernatant liquors of the cell cultures. Table 1 shows that, in the case of the stable recombinant cell clones in accordance with the invention, the cell-specific productivity was stable even after 60 generations in a serum-free and protein-free medium and it had even increased in comparison to the original clone that had been cultivated in a serum-containing medium.

TABLE 1

| Cell Clone | Cell specific productivity of the working cells in mU rvWF/$10^6$ cells/day | Cell specific productivity after 10 generations in mU rvWF/$10^6$ cells/day | Cell specific productivity after 60 generations in mU rvWF/$10^6$ cells/day |
|---|---|---|---|
| rvWF-CHO #808.68 original cell clone | 55 | 30 | <10 |
| r-vWF-CHO F7*) stable clone | 62 | 65 | 60 |

*)filed on Jan. 22, 1998 (ECACC (European Collection of Cell Cultures, Salisbury, Wiltshire SP4 OJG, UK); deposition number 98012206)

Example 4

Composition of a Synthetic Serum Free and Protein-Tree Medium.

TABLE 2

| Component | g/L | Preferred quantity (according to our knowledge at the time of the patent application) in g/L |
|---|---|---|
| Synthetic minimal medium (DMEM/HAM's F12) | 1-100 | 11.00-12.00 |
| Soy peptone | 0.5-50 | 2.5 |
| L-glutamine | 0.05-1 | 0.36 |
| Ascorbic acid | 0.0005-0.05 | 0.0035 |
| NaHCO$_3$ | 0.1-10 | 2.00 |
| Ethanolamine | 0.0005-0.05 | 0.0015 |
| Na selenite | 1-15 µg/l | 8.6 µg/l |

TABLE 2-continued

| Component | g/L | Preferred quantity (according to our knowledge at the time of the patent application) in g/L |
|---|---|---|
| Optionally: Synperonic F68 | 0.01-10 | 0.25 |

Example 5

Cultivation of rFVIII-CHO Cells in a Protein Free and Serum Free Minimal Medium.

A cell culture containing rFVIII-CHO cells was cultivated in a 10-L stirred tank with perfusion. A medium in accordance with Example 4 was used in this case. The cells were thereby immobilized on a porous microcarrier (Cytopore®, Pharmacia) and then cultivated for at least 6 weeks. The perfusion rate was 4 volume changes per day; the pH was 6.9-7.2; the 02 concentration was approximately 20-50% and the temperature was 37° C.

Figure 1B:
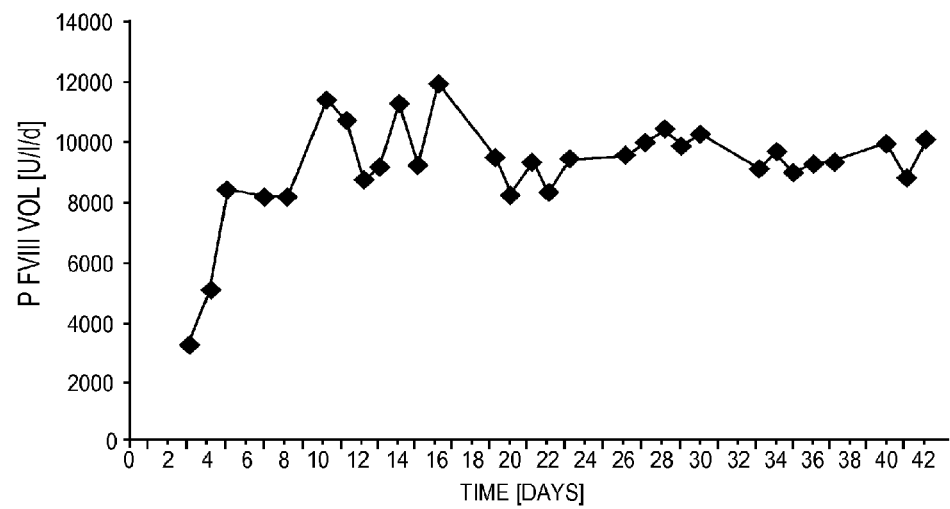
Figure 2:
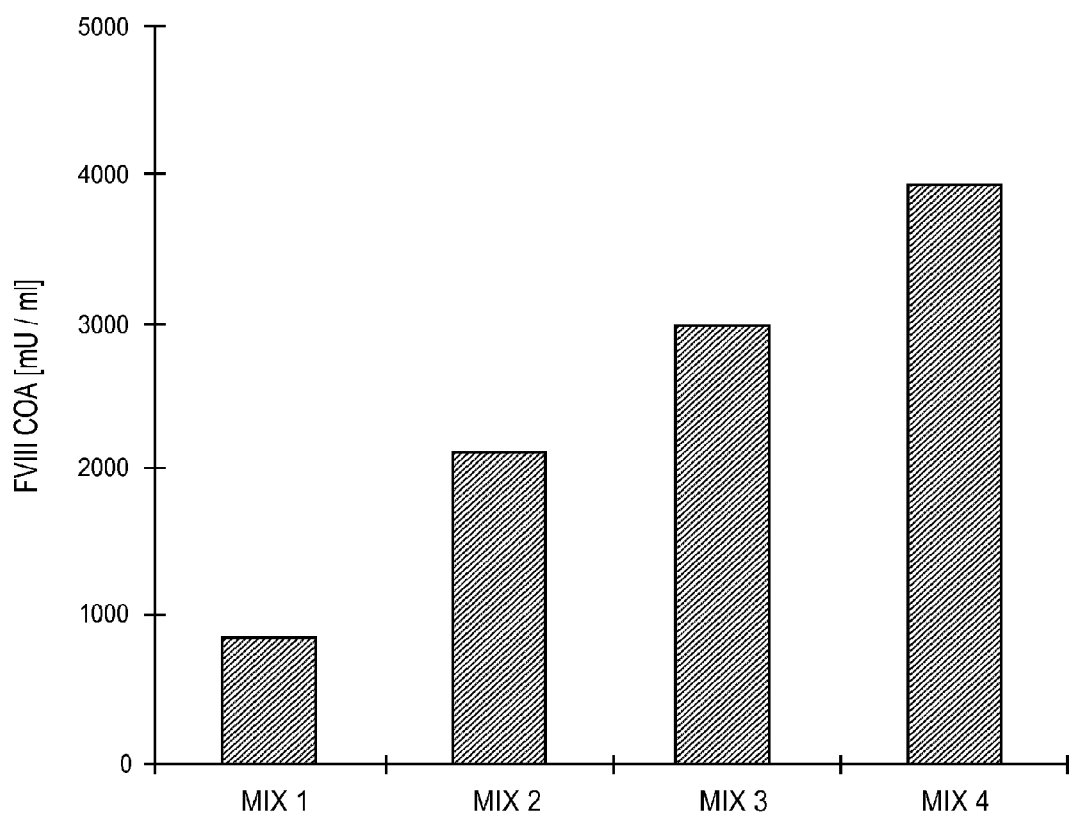
FIG. 2 shows a comparison of the Factor VIII productivity (mU/mL) in the case of cultivation, using the batch process, of CHO cells which express rFactor VIII, in various media. Mix 1 consists of serum-free and protein-free medium without soy hydrolysate, but containing an amino acid mixture as listed in table 4; Mix 2 consists of serum-free and protein-free medium containing soy hydrolysate; Mix 3 consists of serum-free and protein-free medium containing soy hydrolysate and an amino acid mixture as listed in table 4 and Mix 4 consists of serum-free and protein-free medium containing 2.5 g/l purified, ultrafiltrated soy hydrolysate and an amino acid mixture as listed in table 4. For the purification of the ultrafiltrated soy hydrolysate a Sephadex® column was used.
Figure 3:
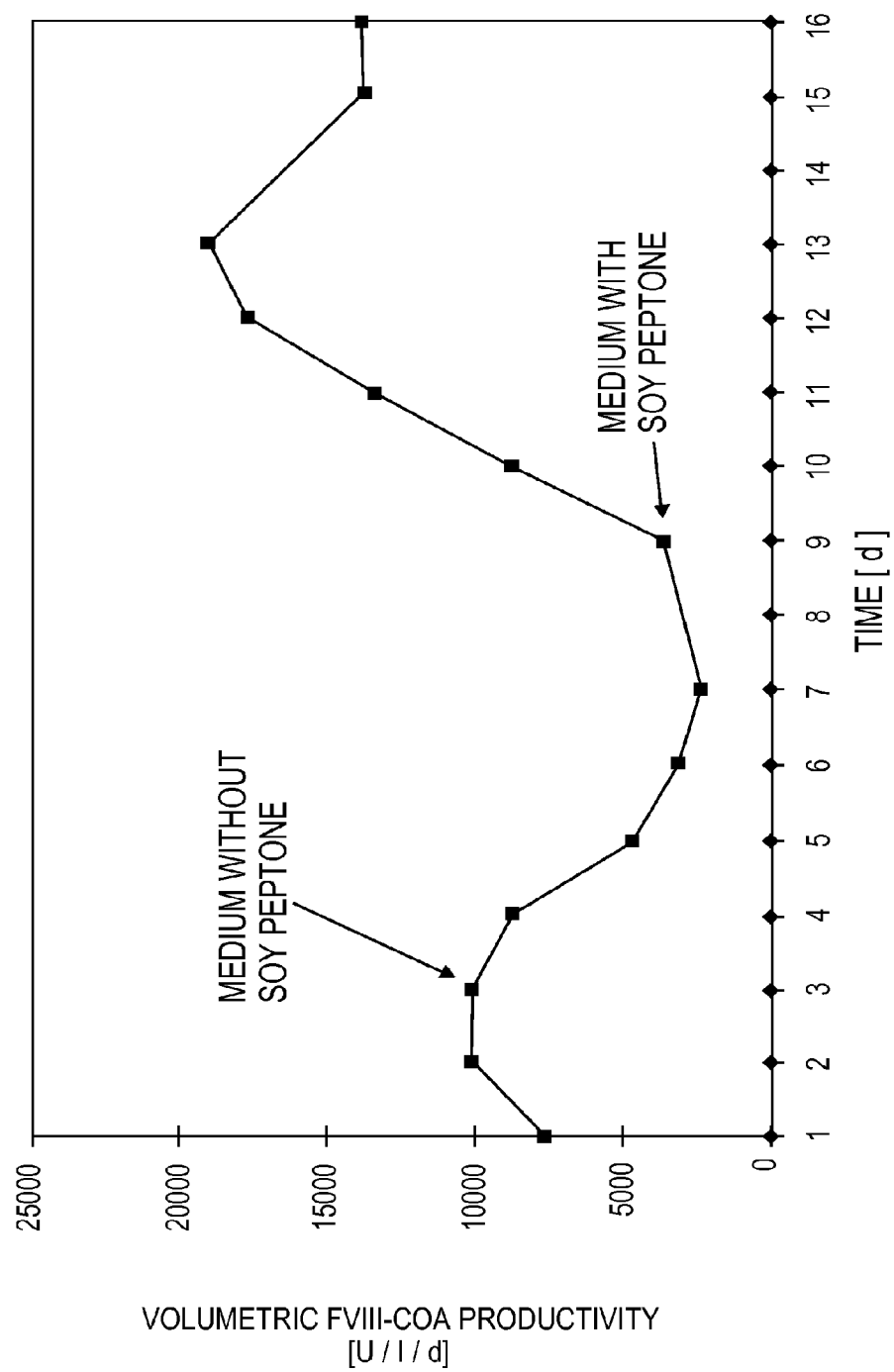
FIG. 3 shows the Factor VIII productivity (U/L) in the case of the continuous growth of CHO cells, which express rFactor VIII, in a serum-free and protein-free medium after the start of the addition of purified, ultrafiltered soy peptone, namely on the 6th day of cultivation.
Figure 4:
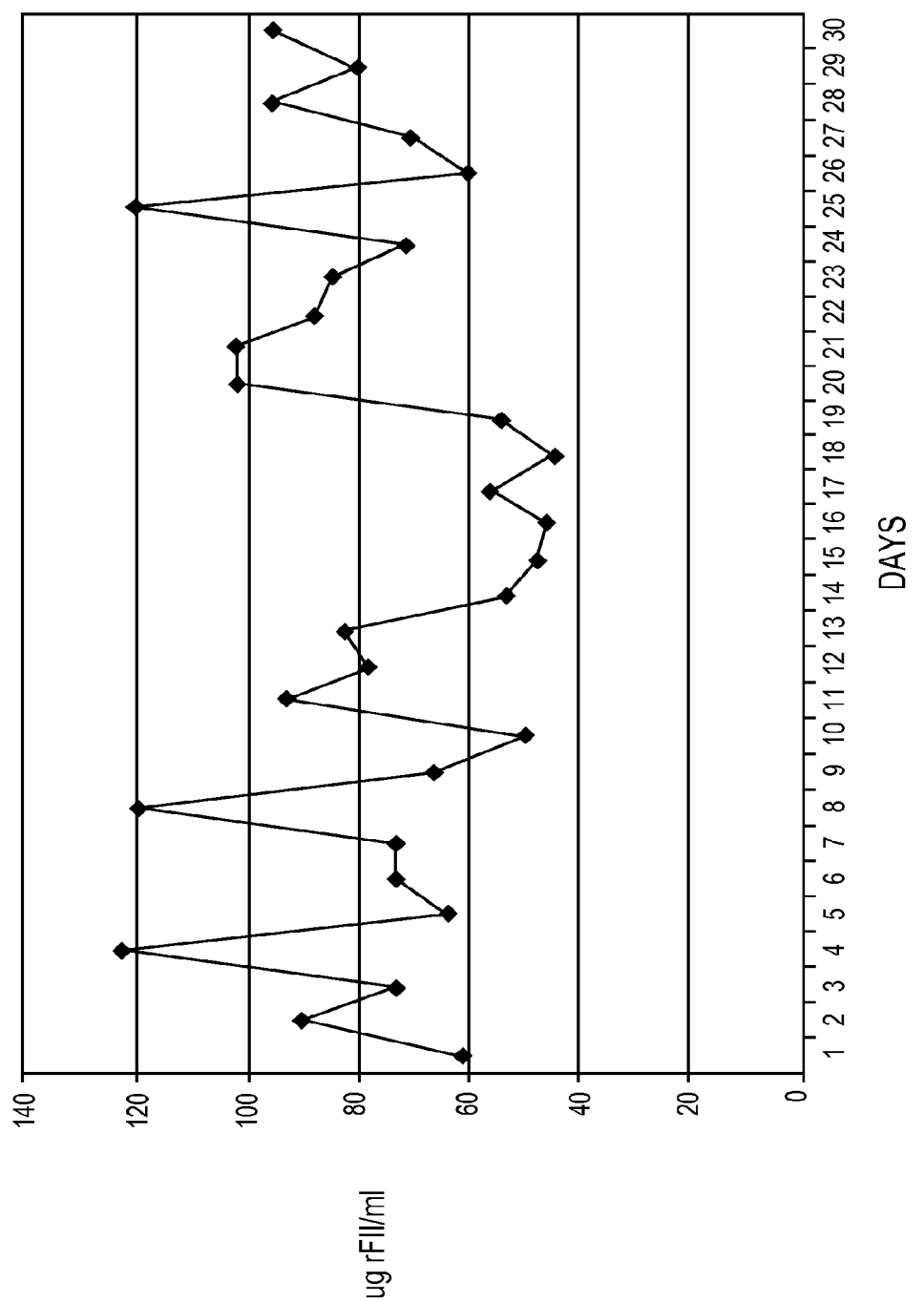
FIG. 4 shows BHK cells expressing recombinant Factor II that have been bred in a protein-free and serum-free medium that contains soy hydrolysate.

FIGS. 1A-1B show the results of the cultivation of a rFVIII-CHO cell clone in a 10 L perfusion bioreactor.

a) Factor VIII activity (milliunits/mL) and perfusion rate (1-5/day) over a period of 42 days.

b) Volumetric productivity (units of Factor VIII/L/day) in the perfusion bioreactor.

TABLE 3

| Days of cultivation | Cell specific productivity (mU/$10^6$ cells/day) | Immunofluorescence (% FVIII positive cells) |
|---|---|---|
| 15 | 702 | n.a. |
| 21 | 1125 | n.a. |
| 28 | 951 | >95% |
| 35 | 691 | >95% |
| 42 | 970 | n.a. |

Table 3 shows the stability and specific productivity of the rFVIII-expressing cells. In order to obtain these results, samples were taken after 15, 21, 26, 35 and 42 days and then centrifuged at 300 g and resuspended in fresh serum-free and protein-free medium. The Factor VIII concentration in the supernatant liquors of the cell cultures and the cell count was determined after a further 24 h. The specific FVIII productivity was 'calculated from these data.

A stable average productivity of 866 milliunits/$10^6$ cells/day was achieved. This stable productivity was also confirmed by immunofluorescence with labelled anti-FVIII antibodies after 15, 21, 29, 35 and 42 days in a serum-free and protein-free medium.

Example 6

Comparison of the Productivity of Recombinant FVIII-CHO Cells in a Protein Free and Serum Free Medium Containing Further Medium Components.

A cell culture containing rFVIII-CHO cells was cultivated batchwise. In this case, use was made of a medium in accordance with Example 4 to which the following amino acids had been added:

TABLE 4

| Amino acid: | mg/l | Preferred quantity (according to our knowledge at the time of the patent application) in mg/L |
|---|---|---|
| L-Asparagine | 1-100 | 20 |
| L-Cysteine•HCl•H$_2$O | 1-100 | 15 |
| L-Cystine | 1-100 | 20 |
| L-Proline | 1-150 | 35 |
| L-Glutamine | 50-1000 | 240 |

The cells were bred at 37° C. and pH 6.9-7.2. The cells were bred using the batch process over periods of 24-72 h.

The productivity of the recombinant FVIII-CHO cells was measured in the following medium compositions:

Mix 1: comprising a serum-free and protein-free medium without soy peptone and additionally containing an amino acid mixture in accordance with the table designated above.

Mix 2: comprising a serum-free and protein-free medium containing soy peptone.

Mix 3: comprising a serum-free and protein-free medium containing soy peptone and additionally containing an amino acid mixture in accordance with the table designated above.

Mix 4: comprising a serum-free and protein-free medium, and additionally containing an amino acid mixture in accordance with the table designated above and 2.5 g/L of purified, ultrafiltered soy peptone. The purification of the ultrafiltered soy peptone took place chromatographically over a Sephadex™ column.

Example 7

Cultivation of Recombinant FVIII-CHO Cells in a Protein Free and Serum-Free Medium Using the Chemostat Culture Method.

A cell culture containing rFVIII-CHO cells was cultivated in a 10-L stirred bioreactor tank. In this case, use was made of a medium in accordance with Example 4, without soy peptone, containing an amino acid mixture in accordance with Example 6. The cells were bred at 37° C. and pH 6.9-7.2; the oxygen concentration was 20-50% air saturation. Samples were taken every 24 h in order to determine the Factor VIII titer and the cell concentration in the supernatant liquor of the culture. The total cell concentration was constant from the 2nd day to the 14th day. Ultrafiltered soy peptone was added to the medium starting from the 6th day. The Factor VIII productivity, is illustrated in 3; the measurements took place by means of a CHROMOGENIX CoA FVIII:C/4 system.

Immunofluorescence was carried out with labelled anti-FVIII antibodies. It can be seen from the data that a distinct increase in Factor VIII productivity and hence an increase in the volumetric productivity of the bioreactor system, occurred as a result of the addition of soy peptone, whereby this did not lead to a distinct increase in cell growth. The absence of soy peptone in the continuous culture leads to a distinct decline in Factor VIII productivity after a few days, whereas the addition of soy peptone leads, as a consequence, to an almost 10-fold increase in productivity. However, since this addition does not increase the cell count, it is hereby clearly shown that ultrafiltered soy peptone leads, as a consequence, to a distinct increase in productivity which is independent of cell growth.

Example 8

Comparison of the Growth Rate and the Productivity of Recombinant FVIII-CHO Cells in a Protein Free and Serum Free Medium Containing Different Hydrolysates.

A rFVIII-CHO cell culture was cultivated batchwise. In this case, use was made of a serum-free and protein-free medium as described in Example 4 to which different hydrolysates (from soy, yeast, rice and wheat) had been added. A serum-free and protein-free medium, to which no hydrolysate had been added, was used as the control.

The initial cell density was 0.6×10$^5$ and 0.4×10$^6$, respectively. The cells were cultured at 37° C. using the batch process at pH 6.9-7.2.

Table 5: shows the results of the cultivation experiments with rFVIII-CHO cells in a serum-free and protein-free medium to which soy hydrolysate (ultrafiltered) and yeast hydrolysate had been added. The initial cell density was 0.6×10$^5$ cells. A serum-free and protein-free medium without hydrolysate additions was used as the control.

TABLE 5

| Hydrolysate | Final cell density (×10$^6$/mL) | FVIII titer (mU/mL) | FVIII clotting activity (mU/mL) |
|---|---|---|---|
| Soy | 3.6 | 485 | 508 |
| Yeast | 3.3 | 226 | 230 |

Table 6: shows the results of the cultivation experiments with rFVIII-CHO cells in a serum-free and protein-free medium to which soy hydrolysate (ultrafiltered), rice hydrolysate and wheat hydrolysate had been added. The initial cell density was 0.6×10$^5$ cells. A serum-free and protein-free medium without hydrolysate additions was used as the control.

TABLE 6

| Hydrolysate | Final cell density (×10$^6$/mL) | FVIII titer (m/U/mL) | VWF - Antigen (µg/mL) |
|---|---|---|---|
| Soy | 3.7 | 1142 | 6.7 |
| Rice | 3.0 | 479 | 3.2 |
| Wheat | 3.4 | 522 | 3.9 |
| Control | 3.0 | 406 | 3.1 |

Table 7 shows the results of the cultivation experiments with rFVIII-CHO cells in a serum-free and protein-free medium to which soy hydrolysate (ultrafiltered) and wheat hydrolysate had been added. The initial cell density amounted to 0.4×10$^6$ cells.

TABLE 7

| Hydrolysate | Final cell density (×10$^6$/mL) | FVIII titer (mU/mL) | FVIII- Antigen (µg/mL) | VWF- Antigen (µg/mL) |
|---|---|---|---|---|
| Soy | 1.6 | 1427 | 166 | 17.2 |
| Wheat | 1.0 | 1120 | 92 | 7.9 |

Example 9

Cultivation of BHK Cells in a Protein Free and Serum Free Medium Containing Soy Hydrolysate.

BHK-21 (ATCC CCL 10) cells were co-transfected three times with the following plasmids by means of a CaPO$_4$ procedure: 25 µg of the plasmid pSV-FII (Fischer, B. et al., J. Biol. Chem., 1996, Vol. 271, pp. 23737-23742) which contains the human Factor II (prothrombin)-cDNA under the control of a SV40 promotor (SV40 early gene promoter); 4

µg of the plasmid pSV-DHFR for methotrexate resistance and 1 µg of the plasmid pUCSV-neo (Schlokat, U. et al., Biotech. Appl. Biochem., 1996, Vol. 24, pp. 257-267) which mediates G418/neomycin resistance. Stable cell clones were selected by means of cultivation in a medium, which contained 500 µg/mL of G418, by increasing the methotrexate concentration in a stepwise manner up to a concentration of 3 µM.

The clones that were obtained in this way were subcloned and adapted to a protein-free and serum-free medium. Cultivation took place using the suspension culture technique.

The results can be seen in Table 6; the BHK cells, which were bred in the protein-free and serum-free medium containing—soy hydrolysate, exhibited a high and stable rate of production of recombinant Factor II.

What is claimed is:

1. A method for increasing productivity of a recombinant protein in a cell culture, the method comprising:
    culturing mammalian cells that express the recombinant protein in an animal protein-free and serum-free cell culture medium; and
    adding more than 10 wt. % ultrafiltered soy hydrolysate based on the total dry weight of the medium to the animal protein-free and serum-free cell culture medium,
wherein at least 40% of the soy hydrolysate has a molecular weight of ≤500 daltons.

2. The method of claim 1, wherein at least 50% of the soy hydrolysate has a molecular weight of ≤500 daltons.

3. The method of claim 1, wherein at least 55% of the soy hydrolysate has a molecular weight of ≤500 daltons.

4. The method of claim 1, wherein the soy hydrolysate has an endotoxin content of <500 U/g.

5. The method of claim 1, wherein the mammalian cells are CHO cells or BHK cells.

6. The method of claim 1, wherein the recombinant protein is selected from the group consisting of: Factor II, Factor V, Factor VII, Factor VIII, Factor IX, Factor X, Factor XI, Protein S, Protein C, activated forms of these factors, and vWF.

7. The method of claim 6, wherein the recombinant protein is Factor VIII.

8. The method of claim 1, wherein the medium comprises an amino acid.

9. The method of claim 8, wherein the amino acid is selected from the group consisting of L-asparagine, L-cysteine, L-cystine, L-proline, L-tryptophan, L-glutamine and mixtures thereof.

10. The method of claim 1, wherein the medium further comprises: 1 to 100 g/L synthetic minimal medium; 0.05-1 g/L glutamine; 0.0005-0.05 g/L ascorbic acid; 0.1-10 g/L $NaHCO_3$; 0.0005-0.05 g/L ethanolamine; and 1-15 µg/L sodium selenite.

11. The method of claim 1, wherein the cells are cultured in a bioreactor.

* * * * *